(12) United States Patent
Naya et al.

(10) Patent No.: US 8,023,115 B2
(45) Date of Patent: Sep. 20, 2011

(54) SENSOR, SENSING SYSTEM AND SENSING METHOD

(75) Inventors: Masayuki Naya, Kanagawa-ken (JP); Takeharu Tani, Kanagawa-ken (JP)

(73) Assignee: FUJIFILM Corporation, Tokyo (JP)

( * ) Notice: Subject to any disclaimer, the term of this patent is extended or adjusted under 35 U.S.C. 154(b) by 295 days.

(21) Appl. No.: 12/306,122

(22) PCT Filed: Jun. 22, 2007

(86) PCT No.: PCT/JP2007/063054
§ 371 (c)(1),
(2), (4) Date: Dec. 22, 2008

(87) PCT Pub. No.: WO2007/148833
PCT Pub. Date: Dec. 27, 2007

(65) Prior Publication Data
US 2009/0268205 A1    Oct. 29, 2009

(30) Foreign Application Priority Data
Jun. 22, 2006  (JP) .................................. 2006-172491

(51) Int. Cl.
*G01N 21/55* (2006.01)
(52) U.S. Cl. ....................................................... 356/445
(58) Field of Classification Search .................. 356/436, 356/454, 480, 517, 519
See application file for complete search history.

(56) References Cited

U.S. PATENT DOCUMENTS

| | | | |
|---|---|---|---|
| 6,639,712 B2 | 10/2003 | McBride et al. | |
| 7,403,292 B2 * | 7/2008 | Tomaru | 356/517 |
| 2004/0183176 A1 | 9/2004 | Naya et al. | |
| 2009/0213384 A1 * | 8/2009 | Naya et al. | 356/450 |
| 2010/0196920 A1 * | 8/2010 | Lee et al. | 435/7.1 |

FOREIGN PATENT DOCUMENTS

| | | |
|---|---|---|
| JP | 2000-356587 A | 12/2000 |
| JP | 2004-232027 A | 8/2004 |
| JP | 2004-279364 A | 10/2004 |
| JP | 2004-533635 A | 11/2004 |
| JP | 2005-265479 A | 9/2005 |

OTHER PUBLICATIONS

Chinese Office Action corresponding to Chinese Patent Application No. 200780022628.X dated Apr. 15, 2010.
J. Haglmuller et al., "Resonant nano-cluster devices", IEE Proceedings Nanobiotechnology, Apr. 2005, pp. 53-62, vol. 152, No. 2.
Second Chinese Office Action for Application No. 200780022628.X, issued Feb. 16, 2011, English Translation.

* cited by examiner

*Primary Examiner* — Roy M Punnoose
(74) *Attorney, Agent, or Firm* — Sughrue Mion, PLLC

(57) ABSTRACT

A sensor is an optical resonator constituted by: a first reflecting body that exhibits semi transmissivity/semi reflectivity; a transparent body; and a second reflecting body that exhibits one of reflectivity and semi transmissivity/semi reflectivity, provided in this order from the light incident side. The sensor is configured such that the absorption peak of the measuring light beam by resonance in the optical resonator matches the absorption peak of the measuring light beam by local plasmon resonance generated at the surface and/or within the optical resonator. The sensor has absorption properties such that light of specific wavelengths are absorbed depending the mean complex refractive indices of the first and second reflecting bodies and the thickness of the transparent body. An emitted light beam is output from the first reflecting body. The physical properties of the emitted light beam that change according to the absorption properties are detected.

14 Claims, 7 Drawing Sheets

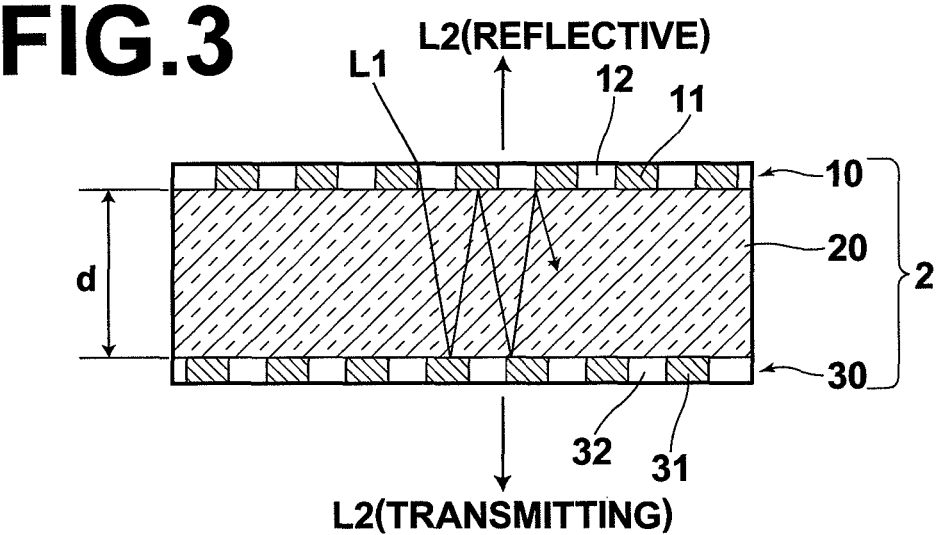
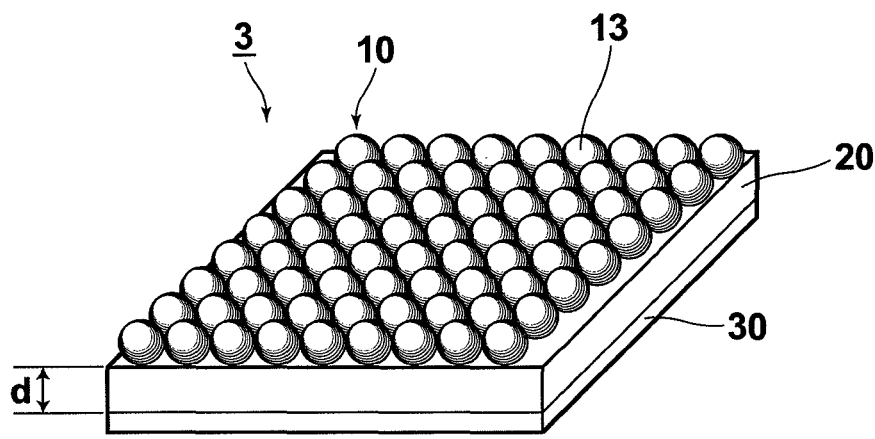
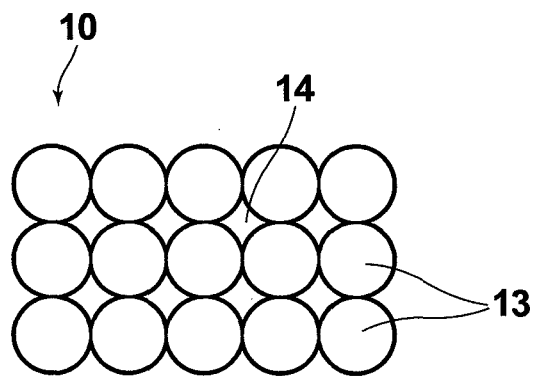

SENSOR, SENSING SYSTEM AND SENSING METHOD

FIELD OF THE INVENTION

This invention relates to a sensor which emits measuring light incident into a sample as emitted light having physical properties different according to the sample, and a sensing system and a sensing method employing the same.

BACKGROUND OF THE INVENTION

As a sensor for use in analysis of an organic molecule, there has been proposed a sensor utilizing a phenomenon where reflected light of a particular wavelength is attenuated in intensity by a local plasmon resonance. It is said that though being simple in structure and less expensive and smaller in structural limitation, the local plasmon sensor is not excellent in detecting sensitivity and it is difficult to carry out a precision analysis by the use of the local plasmon sensor. Since the detecting sensitivity is influenced by the in-plane uniformity of recessed/projected structure (sometimes referred to as "an irregularity") of the metal fine structure in the sensor surface, there has been proposed a method in which the recessed/projected structure of the metal fine structure is precisely controlled to produce a metal fine structure which is high in the regularity of the recessed/projected structure. See, for instance, Japanese Unexamined Patent Publication Nos. 2004-279364 and 2004-232027.

DISCLOSURE OF THE INVENTION

In the plasmon sensors disclosed in Japanese Unexamined Patent Publication Nos. 2004-279364 and 2004-232027, the metal fine structure is produced on the basis of a metal fine structure which is high in the regularity of the recessed/projected structure obtained by anodizing metal and accordingly they can relatively easily control the fine structure. However, since the absorption peak of the local plasmon includes scattered light in the metal fine structure which influences the effect of absorption to broaden the peak width, and a sufficient sensitivity cannot be obtained, it is difficult to carry out a precision analysis by the use of the local plasmon sensor.

In view of the foregoing observations and description, the primary object of the present invention is to provide a novel sensor which is better in detecting sensitivity as compared with the plasmon sensor while having a relatively simple structure.

Another object of the present invention is to provide a sensing system and a sensing method by the use of such a novel sensor.

In accordance with the present invention, there is provided a sensor which emits measuring light incident into a sample as emitted light having physical properties different according to the sample comprising an optical resonator where a first reflecting body which exhibits a semi-transmissivity/semi-reflectivity, a transparent body and a second reflecting body which has a reflectivity or a semi-transmissivity/semi-reflectivity are laminated in sequence one on another, the measuring light absorption peak by a resonance in the optical resonator conforming to that by a local plasmon resonance generated on the surface and/or inside of the optical resonator.

In this specification, the "semi-transmissivity/semi-reflectivity" means to have both the transmissivity and the reflectivity and the transmittance and the reflectance may be arbitrary.

In the sensor of the present invention, it is preferred that the first and/or second reflecting bodies have recessed/projected structure which is smaller than the wavelength of the measuring light.

The expression "recessed/projected structure which is smaller than the wavelength of the measuring light" as used here means that the average size (the "size" as used here means "a maximum width") of the projected parts and the recessed parts (the "recessed parts" as used here includes a space extending through the reflecting body in the direction of thickness) and the average pitches of the projected parts and the recessed parts are smaller than the wavelength of the measuring light.

As a preferred embodiment of the sensor of the present invention, there can be shown that in which the first and/or second reflecting bodies are a metal layer formed in a pattern on the surface of the transparent body.

As another preferred embodiment of the sensor of the present invention, there can be shown that in which the first and/or second reflecting bodies are a metal layer formed by a plurality of metal particles fixed to the surface of the transparent body.

As still another preferred embodiment of the sensor of the present invention, there can be shown that in which the transparent body comprises a transparent fine hole body having a plurality of fine holes which open in a surface facing the first reflecting body and are smaller than the wavelength of the measuring light in diameter and the first reflecting body is a metal layer having a plurality of fine holes along the surface of the transparent body. In such a structure, a part of the fine holes may be filled with metal or only a bottom of the fine holes may be filled with metal.

The sensing system of the present invention comprises a sensor of the present invention described above, a light projecting means which projects the measuring light onto the sensor and a detector which detects physical properties of light emanating from the sensor.

As a detector, those which detects at least one of the intensity, the rate of change of the intensity and the physical properties of the emitted light from the sensor are preferable.

In the sensing system of the present invention, the refractive index and/or the concentration of a sample can be analyzed and the sample can be identified by analyzing the refractive index of the sample.

The sensing method of the present invention comprises the steps of bringing a sample into contact with a sensor of the present invention after bringing a bonding material which specifically bonds with specific material into contact with a contact side of the sensor, projecting measuring light onto the sensor and detecting physical properties of light emanating from the sensor, whereby existence and/or a quantity of the specific material in the sample are analyzed.

The sensor of the present invention comprises an optical resonator where a first reflecting body which exhibits, a transparent body and a second reflecting body which has a reflectivity or a semi-transmissivity/semi-reflectivity are laminated in sequence one on another, the measuring light absorption peak by a resonance in the optical resonator conforming to that by a local plasmon resonance generated on the surface and/or inside of the optical resonator.

With this arrangement, light having a reflection peak due to local plasmon resonance is emitted from the first and/or second reflecting bodies. The resonating conditions and the local plasmon resonant wavelength change with contact of the sample, and the physical properties of the emitted light change in a similar manner in response thereto. Accordingly, the sample can be analyzed by detecting the intensity, the wavelength shift and the like.

It has been known that the reflection peak is generally higher in S/N ratio as compared with the absorption peak. Accordingly, in accordance the present invention, since the sensing can be done by the reflection peak having a high S/N ratio, a sensitive sensor which is excellent in sensitivity as compared with the local plasmon sensor can be provided.

BRIEF DESCRIPTION OF THE DRAWINGS

FIG. 3 is a cross-sectional view in the direction of thickness of a sensor in accordance with a second embodiment of the present invention, FIG. 4A is a perspective view of a sensor in accordance with a third embodiment of the present invention, FIG. 4B is a plan view of the same.

PREFERRED EMBODIMENTS OF THE INVENTION

First Embodiment of the Sensor

Figure 1A:
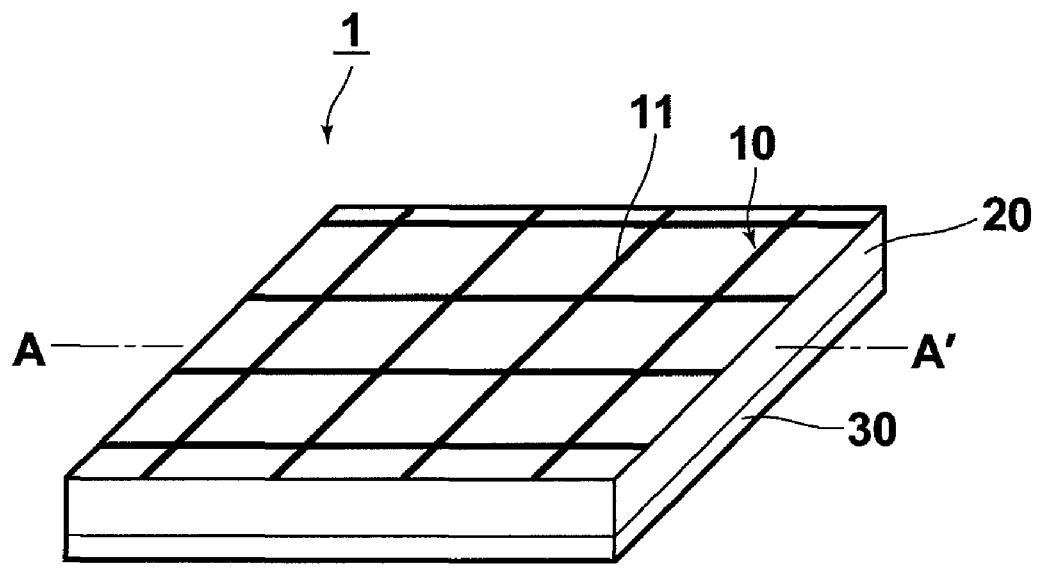
FIG. 1A is a perspective view of a sensor in accordance with a first embodiment of the present invention.

A sensor in accordance with a first embodiment of the present invention will be described with reference to FIGS. 1A and 1B, hereinbelow. FIG. 1A is a perspective of the first embodiment and FIG. 1B is a cross-sectional view in the direction of the thickness (taken along line A-A') of the same.

Figure 1B:
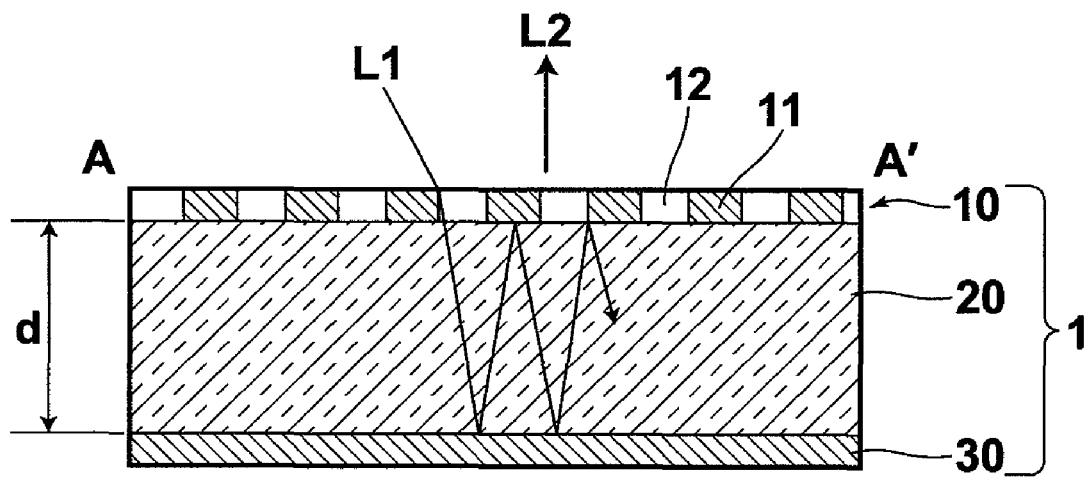
FIG. 1B is a cross-sectional view in the direction of thickness of the same.

As shown in FIGS. 1A and 1B, the sensor 1 in accordance with this embodiment comprises in sequence, from the incident side (from upward in FIGS. 1A and 1B) of measuring light L1, a first reflecting body 10 which exhibits semi-transmissivity/semi-reflectivity, a transparent body 20 and a second reflecting body 30 which has a reflectivity. The measuring light L1 may be either mono-wavelength light or broad light and the wavelength of the measuring light L1 is selected according to the physical property to be detected.

The transparent body 20 comprises a transparent flat substrate while the first reflecting body 10 comprises a metal layer where fine metal cables 11 are formed in a regular grid pattern on one side of the transparent body 20 and the second reflecting body 30 comprises a solid metal layer formed on the other side of the transparent body 20.

The transparent body 20 may be formed of any suitable material, and for instance, may be formed of a transparent ceramics such as glass or alumina or a transparent resin such as acrylic resin or polycarbonate resin.

The first and second reflecting bodies 10 and 30 may be formed of any suitable reflective metal and may be formed of Au, Ag, Cu, Al, Pt, Ni, Ti or their alloys. The first and second reflecting bodies 10 and 30 may include not smaller than two kinds of these reflective metals.

The second reflecting body 30 which is a solid metal layer can be formed by, for instance, a metal vapor deposition. The first reflecting body 10 can be formed, for instance, by carrying out the known photolithography after a solid metal layer is formed by, for instance, the metal vapor deposition.

The first reflecting body 10 exhibits a light transmissivity since it has a plurality of patterned voids 12 though formed of reflective metal and after all exhibits a semi-transmissivity/semi-reflectivity. The line width and the pitches of the fine metal cable 11 of the first reflecting body 10 are smaller than the wavelength of the measuring light L1, and the first reflecting body 10 has a recessed/projected structure smaller than the wavelength of the measuring light L1. When the recessed/projected structure is smaller than the wavelength of the light, the first reflecting body 10 behaves as film to light and exhibits a semi-transmissivity/semi-reflectivity having an electromagnetic mesh shielding function.

The sensor 1 in accordance with this embodiment is a sensing body, where average complex refractive indexes of the first and second reflecting bodies 10 and 30 change according to the sample in contact therewith, and the sample can be analyzed by placing a sample in contact with the first and second reflecting bodies 10 and 30.

Since, especially the first reflecting body 10 has a recessed/projected structure smaller than the wavelength of the measuring light L1, the change in the average complex refractive index takes place in the first reflecting body 10 at a higher sensitivity than in the second reflecting body 30. This is believed because of, for instance, vibration of the measuring light L1 effectively generated in the first reflective body 10 in the recessed/projected structure thereof.

The pitches of the fine metal cable 11 may be any so long as they are smaller than the wavelength of the measuring light L1 and when visible light is employed as the measuring light L1, the pitches of the fine metal cable 11 are preferably not larger than, for instance, 200 nm. The pitches of the fine metal cable 11 may be any and are preferably as small as possible in view of sensitivity. The line width of the fine metal cable 11 may be any and is preferably as small as possible in view of sensitivity. The line width of the fine metal cable 11 is preferably not larger than an average free stroke of the electrons which are vibrated by light, and specifically, the line width of the fine metal cable 11 is preferably not larger than 50 nm and more preferably not larger than 30 nm.

It is preferred that the pitches and the line width of the fine metal cable 11 be preferably as small as possible, since the proportion of the surface of a single fine metal cable 11 is relatively increased, and the surface characteristics of the fine metal cable 11 are more apt to be reflected to the general characteristics of the first reflecting body 10, whereby a higher sensitivity can be obtained. Specifically, as the pitches and the line width of the fine metal cable 11 become smaller, the change of the dielectric constant of the first reflecting body 10 due to difference in samples becomes larger, whereby change of the average complex refractive index (effective complex refractive index) becomes larger, and a higher sensitivity can be obtained.

As shown in FIG. 1B, when the measuring light L1 impinges upon the sensor 1, the measuring light L1 is partly reflected by the surface of the first reflecting body 10 (not shown) and partly passes through the first reflecting body 10 to enter the transparent body 20 according to the transmissivity or the reflectance of the first reflecting body 10. Light entering the transparent body 20 is repeatedly reflected between the first and second reflecting bodies 10 and 30. That is, the sensor 1 is an optical resonator where a multiple reflection takes place between the first and second reflecting bodies 10 and 30.

In such a device, since a multiple interference by multiple reflection light takes place and absorption characteristics is exhibited where light of a particular wavelength satisfying the resonant conditions is selectively absorbed. Since the resonant conditions change according to the average complex refractive index of the first and second reflecting bodies 10 and 30 and the thickness d and the average complex refractive index of the transparent body 20, the device exhibits absorption characteristics where light of a particular wavelength is absorbed according to these factors and emits the emitted light L2 different in its physical properties from the measuring light L1 according to the absorption characteristics. The sensor 1 of this embodiment is a reflective sensor where the emitted light L2 is emitted only from the first reflecting body 10, since the second reflecting body 30 has a reflectivity.

In the sensor 1 of this embodiment, local plasmon resonance is generated in the first reflecting body 10 since the first and second reflecting bodies 10 and 30 are both of metal and the first reflecting body 10 has a fine recessed/projected structure smaller than the wavelength of the measuring light L1.

The local plasmon resonance is a phenomenon that free electrons of metal vibrates in resonance to the electric field of light to generate an electric field. It is said that especially in a metal layer having a fine recessed/projected structure, a strong electric field is generated around projections when free electrons on the projections resonate with the electric field of light and vibrates and the local plasmon resonance effectively takes place. In this embodiment, since the first reflecting body 10 has a recessed/projected structure smaller than the wavelength of the measuring light L1 as described above, the local plasmon resonance effectively takes place.

At the wavelength where the local plasmon resonance is generated, scattering and/or absorption of the measuring light L1 is significantly enhanced, and the intensity of light emanating from the sensor 1 is significantly lowered. The local plasmon resonant wavelength and the degree of scattering and/or absorption of the measuring light L1 depend upon the size of recessed/projected structure on the surface of the sensor 1, the kind of metal, the refractive index of the sample in contact with the surface and the like and accordingly, change with the physical properties of the sample in contact with the surface of the sensor 1.

Though the local plasmon resonance can take place in any metal, as the first reflecting body 10, gold (Au), silver (Ag), copper (Cu), nickel (Ni) or titanium (Ti) is preferable, and gold (Au) and silver (Ag) is especially preferable.

In the sensor 1 of this embodiment, sensing is carried out by a reflection peak generated by superposing the peak of absorption due to the multiple interference described above and the peak of local plasmon resonance. Accordingly, the sensor 1 is designed so that the resonant wavelength ($\lambda r$) by the multiple interference is substantially equal to the local plasmon resonant wavelength ($\lambda r \approx \lambda 1p$).

Though the resonant conditions are influenced also by the average complex refractive indexes ($n_1-ik_1$) and ($n_3-ik_3$) of the first and second reflecting bodies 10 and 30 and the average complex refractive index ($n_2-ik_2$) and the thickness d of the transparent body 20, since the influence of changes in the average complex refractive indexes ($n_1-ik_1$) and ($n_3-ik_3$) of the first and second reflecting bodies 10 and 30 is small as compared with the influence of change in the average complex refractive index ($n_2-ik_2$) and the thickness d of the transparent body 20, the resonant wavelength can be substantially determined by the thickness d of the transparent body 20 up to precision of the order of several nm. ($-ik_1$, $-ik_2$, and $-ik_3$ represent imaginary parts. Since the imaginary part of the average complex refractive index ($n_2-ik_2$) of the transparent body 20 is 0 in this embodiment, $n_2-ik_2=n_2$.) Accordingly, in the sensor 1, the thickness d of the transparent body 20 is optimized so that $\lambda r$ and $\lambda 1p$ conform to each other. When the thickness d of the transparent body 20 is arbitrary, $\lambda r$ and $\lambda 1p$ are sometimes different from each other, and sometimes conform to each other.

The average complex refractive index ($n_2-ik_2$) and the thickness d of the transparent body 20 together with the resonant wavelength $\lambda r$ sufficiently satisfy the following formula at the order of several nm. Accordingly, so long as the average complex refractive index ($n_2-ik_2$) of the transparent body 20 is the same, the resonant wavelength $\lambda r$ can be changed by simply changing the thickness d of the transparent body 20.

$$d=(m+1)\lambda r/2(n_2-ik_2)$$

wherein d represents the thickness of the transparent body 20, $\lambda r$ represents the resonant wavelength, ($n_2-ik_2$) represents average complex refractive index and m represents an integer.

When the transparent body 20 comprises a light transmitting fine hole member as in the fourth embodiment described later, "the average complex refractive index in the transparent body 20" means the average of the complex refractive index in the light transmitting fine hole member and the complex refractive index of the material in the fine holes (when the fine holes are not filled with a particular material, "the material in the fine holes" is air, and when the fine holes are filled with a particular material, "the material in the fine holes" is the particular material in the fine holes and/or a mixture of air and the particular material in the fine holes).

Though the thickness d of the transparent body 20 has a plurality of values according to the value of m in the formula, is preferably not larger than 300 nm in that absorption peak wavelength in a visible wavelength region by the multiple interference is a single and easy to detect, while preferably not smaller than 100 nm in that a multiple reflection effectively takes place, and absorption peak wavelengths by the multiple interference are easy to detect in a visible wavelength region. As described above, though small as compared with the influence by the change in the average complex refractive index ($n_2-ik_2$) and the thickness d of the transparent body 20, since the resonant conditions are influenced also by the average complex refractive indexes ($n_1-ik_1$) and ($n_3-ik_3$) of the first and second reflecting bodies 10 and 30 and the surface condition thereof, the physical properties of the emitted light L2 change in response to contact of the sample with the first and second reflecting bodies 10 and 30.

Figure 2A:
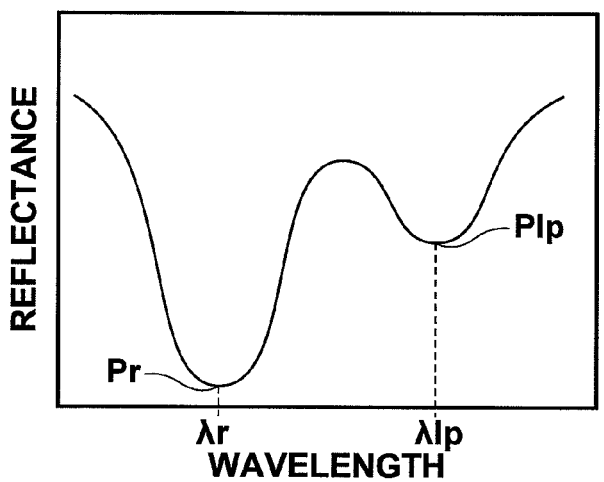
FIG. 2A is an example of a spectrum of the emitted light L2 when the thickness is not optimized in the sensor in accordance with the first embodiment of the present invention.

FIG. 2A shows an example of a spectrum of the emitted light L2 when the thickness d is not optimized ($\lambda r \neq \lambda 1p$) in the sensor 1. In FIG. 2A, absorption peak (Pr) by the multiple interference and the local plasmon resonance absorption peak (P1p) appear at different wavelengths. As shown, the local plasmon resonance absorption peak is generally worse in sensitivity as compared with the absorption peak by the multiple interference.

Figure 2B:
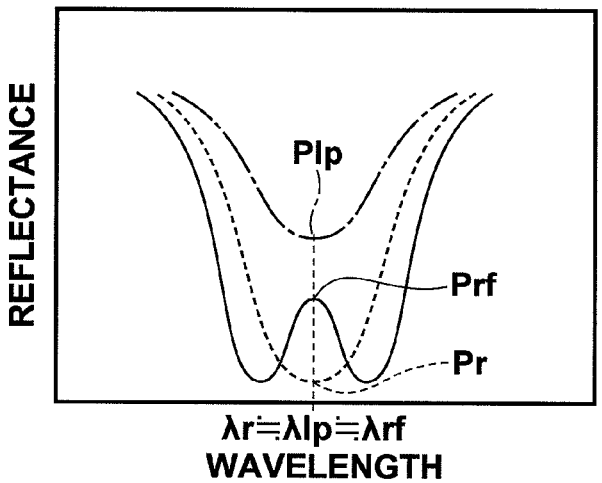
FIG. 2B is an example of a spectrum of the emitted light L2 when the thickness is optimized.

FIG. 2B shows an example of a spectrum of the emitted light L2 when the thickness d is optimized in the sensor 1 so that the absorption peak Pr by the multiple interference is superposed on the local plasmon resonance absorption peak P1$p$. For the purpose of simplicity of understanding, the shape of the original absorption peak is also shown. The spectrum of the emitted light L2 shown in FIG. 2B is W-shaped having a reflection peak Prf in the absorption peaks and the wavelength at the reflection peak Prf is substantially equal to the local plasmon resonant wavelength λ1$p$.

Figure 2C:
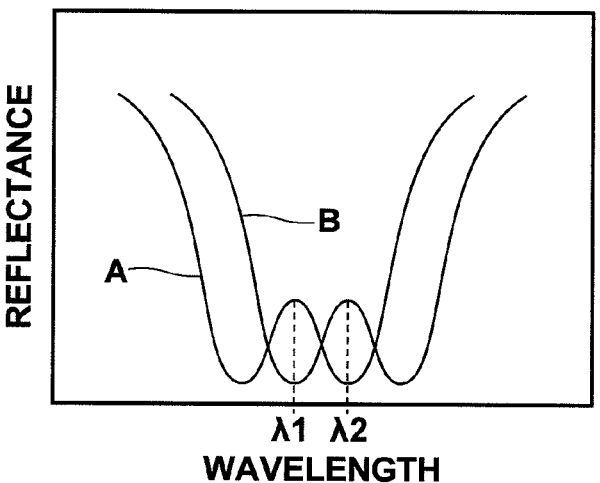
FIG. 2C shows an example of a spectrum change of the emitted light L2 due to contact of a sample.

FIG. 2C shows an example of a spectrum of the emitted light L2 when different samples A and B are brought into contact with the first reflecting body 10 of the sensor 1 and shows the state where the wavelength at the reflection peak Prf changes from λ1 to µ2 by changing the sample. Any of the spectral shown in FIGS. 2A to 2C is when white light is employed as the measuring light L1.

In the sensor 1, it is preferred that the device structure is formed by taking an optical impedance matching so that the number of the multiple reflection (finesse) in the transparent body 20 is maximized. Such arrangement is preferable in that the absorption peaks become sharp and a more precise analysis can be carried out.

In the sensor 1, when the sample is brought into contact with the first and/or second reflecting bodies 10 and 30 (preferably the first reflecting body 10), the average complex index (effective complex index) of the reflecting body in contact with the sample changes by the mutual action of the reflecting body and the sample, and the resonant conditions of the sensor 1 and the local plasmon resonant conditions change, whereby absorption characteristics change and when the absorption characteristics change, the physical properties of the emitted light L2 also change according to the absorption characteristics of the sensor 1. Accordingly, by detecting the physical properties of the emitted light L2 in the sensor 1, the sample can be analyzed.

As the physical properties of the emitted light L2 which change according to the absorption characteristics of the sensor 1, the intensity and the rate of change of intensity of the emitted light L2 and the reflection peak wavelength or the reflection peak wavelength shift can be shown. An example of a specific sensing system will be described later.

In the sensor 1 of this embodiment, the refractive index and/or the concentration of the sample can be analyzed, and the sample can be even identified by analyzing the refractive index of the sample. Further, by bringing the sample into contact with the reflecting body after fixing bonding material, which is specifically bonded with a specific material, to a reflecting body (the first and/or second reflecting bodies 10 and 30) to be brought into contact with the sample, projecting measuring light L1 onto the sensor 1 and detecting the emanating angle 12, existence and/or a quantity of the specific material in the sample can be analyzed. As a combination of the specific material and the bonding material, the combination of the antigen and the antibody (either one of them may be the bonding material), for instance, can be shown. In this embodiment, a time analysis of an antigen/antibody reaction can be done.

The sensor 1 of this embodiment is arranged as described above. The sensor 1 of this embodiment, as described above, comprises an optical resonator where a first reflecting body 10 which exhibits a semi-transmissivity/semi-reflectivity, a transparent body 20 and a second reflecting body 30 which has a reflectivity are laminated in sequence one on another, the measuring light absorption peak Pr by a resonance in the optical resonator conforming to the measuring light absorption peak P1$p$ by a local plasmon resonance generated on the surface of the optical resonator (the first reflecting body 10).

In this arrangement, light entering the transparent body 20 after passing through the first reflecting body 10 is repeatedly reflected between the first and second reflecting bodies 10 and 30 to generate a multiple interference due to a multiple reflection, and absorption characteristics where, a particular wavelength satisfying the resonant conditions are selectively absorbed, are exhibited. Whereas, on the surface of the optical resonator (the first reflecting body 10), a local plasmon resonance due to the recessed/projected structure of the fine metal structure is generated. Since the resonant wavelength λr by the multiple interference can be easily changed by changing the thickness d of the transparent body 20, by causing the resonant wavelength λr and the local plasmon resonant wavelength λ1$p$ to conform to each other by changing the thickness d of the transparent body 20, an emitted light L2 having a reflection peak Prf due to the local plasmon resonance is emitted from the first reflecting body 10.

It has been known that the reflection peak is generally higher in S/N ratio as compared with the absorption peak. Also, in the sensor 1 in accordance the present embodiment, since the background of the reflection peak Prf can be close to 0, the sensing can be done by the reflection peak having a very high S/N ratio. Accordingly, a highly sensitive sensing which is excellent in sensitivity as compared with that by the use of the local plasmon sensor can be done.

Though, the reflection peak Prf generated by superposing the resonant wavelength λr on the local plasmon resonant wavelength λ1$p$ is used, and the reflection peak Prf is due to the local plasmon resonance in this embodiment, as described above, it is conceivable that the reflection peak Prf appears due to the mutual action between the resonance by the multiple interference and the local plasmon resonance or a phenomenon peculiar to the arrangement of the device described above without limited to due to the local plasmon resonance.

Though the case where the first reflecting body 10 is in a regular grid pattern has been described in this embodiment, the first reflecting body 10 is in any pattern and it may be even in a random pattern. However, that the regularity in structure is higher is preferred in that higher the in-plane uniformity of the resonant structure is, and the characteristics are more concentrated.

Second Embodiment of the Sensor

A sensor of a second embodiment of the present invention will be described with reference to FIG. 3, hereinbelow. FIG. 3 is a cross-sectional view similar to FIG. 1A of the first embodiment. In this embodiment, the elements analogous to those in the first embodiment will be given the same reference numerals and will not be described.

As shown in FIG. 3, the sensor 2 in accordance with this embodiment comprises similarly to the first embodiment, in sequence from the incident side (from upward in FIG. 3) of measuring light L1, a first reflecting body 10 which exhibits semi-transmissivity/semi-reflectivity, a transparent body 20 and a second reflecting body 30 which has a semi-transmissivity/semi-reflectivity. The sensor 2 in accordance with this embodiment differs from that in accordance with the first embodiment in that in the second embodiment, the second reflecting body 30 is formed of a metal layer where fine metal cables 11 are formed in a regular grid pattern as the first reflecting body 10 of the first embodiment and exhibits semi-transmissivity/semi-reflectivity whereas, in the first embodiment, the second reflecting body 30 is a reflecting body comprising a solid metal layer and having a reflectivity (the second reflecting body 30 in the second embodiment is the same as that of the second reflecting body 30 in the first embodiment in perspective view).

The sensor 2 in accordance with this embodiment is also a sensing body, where average complex refractive indexes of the first and second reflecting bodies 10 and 30 change according to the sample in contact therewith, and the sample can be analyzed by placing a sample in contact with the first and second reflecting bodies 10 and 30. Since, both the first and second reflecting bodies 10 and 30 have a recessed/projected structure smaller than the wavelength of the measuring light in this embodiment, change in the average complex refractive indexes by the sample takes place at a high sensitivity when the sample is brought into either of the first and second reflecting bodies 10 and 30.

In this arrangement as in the first embodiment, light entering the transparent body 20 after passing through the first reflecting body 10 is repeatedly reflected between the first and second reflecting bodies 10 and 30 to generate a multiple interference due to a multiple reflection, and absorption characteristics where, a particular wavelength satisfying the resonant conditions are selectively absorbed are exhibited.

In this embodiment, a local plasmon resonance is generated in also the second reflecting body 30 since the first and second reflecting bodies 10 and 30 both have a fine recessed/projected structure smaller than the wavelength of the measuring light L1. Accordingly, in this embodiment, the local plasmon resonance due to fine metal recessed/projected structure is generated on the surface and inside of the optical resonator (the first and second reflecting bodies 10 and 30).

Also in this embodiment, since the resonant wavelength $\lambda r$ by the multiple interference can be easily changed by changing the thickness d of the transparent body 20, by causing the resonant wavelength $\lambda r$ and the local plasmon resonant wavelength $\lambda 1p$ to conform to each other by changing the thickness d of the transparent body 20, an emitted light L2 having a reflection peak Prf due to the local plasmon resonance is emitted from the first and second reflecting bodies 10 and 30.

When the sample is brought into contact with the first and/or second reflecting bodies 10 and 30, the average complex index (effective complex index) of the reflecting body in contact with the sample changes by the mutual action of the reflecting body and the sample. Accordingly, even when the second reflecting body 30 has a semi-transmissivity/semi-reflectivity, the sample can be analyzed by detecting the physical properties of the emitted light L2 changing according to the absorption characteristics.

In the first embodiment where the second reflecting body 30 has only a reflectivity, only the reflective sensor is obtained. Whereas in this embodiment where the second reflecting body 30 has a semi-transmissivity/semi-reflectivity, one of a reflective sensor where the emitted light L2 is emitted only from the first reflecting body 10, a transmitting sensor where the emitted light L2 is emitted only from the second reflecting body 30, and a semi-transmitting/semi-reflective sensor where the emitted light L2 is emitted from the first and second reflecting bodies 10 and 30, the emitted light L2 being emitted according to the average complex refractive indexes of the first and second reflecting bodies 10 and 30, and the average complex refractive index and the thickness d of the transparent body 20 in each case. In any sensor, an example of spectrum of the emitted light L2 emitted from the first and second reflecting bodies 10 and 30 is similar to that emitted from the first reflecting body 10.

The sensor 2 of this embodiment is basically the same as the first embodiment except that the second reflecting body 30 has a semi-transmissivity/semi-reflectivity and accordingly, exhibits the same effect as the first embodiment. Though, in this embodiment, the first and second reflecting bodies 10 and 30 are arranged in the same patterns, they may be arranged in different patterns.

Third Embodiment of the Sensor

A sensor of a third embodiment of the present invention will be described with reference to FIGS. 4A and 4B, hereinbelow.

FIG. 4A is a perspective view corresponding to FIG. 1A of the first embodiment and FIG. 4B is a plan view showing the sensor. In this embodiment, the elements analogous to those in the first embodiment will be given the same reference numerals and will not be described.

As shown in FIG. 4A, the sensor 3 in accordance with this embodiment comprises similarly to the first embodiment, in sequence from the incident side of measuring light L1, a first reflecting body 10 which exhibits semi-transmissivity/semi-reflectivity, a transparent body 20 and a second reflecting body 30 which has a reflectivity.

The sensor 3 in accordance with this embodiment differs from that in accordance with the first embodiment in that in the third embodiment, the first reflecting body 10 is formed of a metal layer where a plurality of metal particles 13 substantially equal to each other in diameter were substantially regularly arranged in matrix on the surface of transparent body 20 whereas, in the first embodiment, the first reflecting body 10 is formed of a metal layer formed in a pattern. The metal particles 13 may be formed of any suitable material and as the material for the metal particles 13, those for the first reflecting body 10 in the first embodiment may be shown.

Further, the first reflecting body 10 can be formed by, for instance, applying dispersion of the metal particles 13 by spin coating or the like to the surface of the transparent body 20, and drying it. It is preferred that the dispersion includes a binder such as resin or protein so that the metal particles 13 are fixed to the surface of the transparent body 20 by way of the binder. When protein is employed as the binder, it is possible to fix the metal particles 13 to the surface of the transparent body 20 by the use of the bonding reaction between the proteins.

The first reflecting body 10 exhibits a light transmissivity since it has a plurality of inter-particle spaces 14 which are void though formed of reflective metal and after all exhibits a semi-transmissivity/semi-reflectivity. The diameter and the pitch of the metal particles 13 are designed to be smaller than the wavelength of the measuring light L1, and the first reflecting body 10 has an irregularity smaller than the wavelength of the measuring light L1. Since being smaller than the wavelength of the light, the first reflecting body 10 behaves as film to light and exhibits a semi-transmissivity/semi-reflectivity having an electromagnetic mesh shielding function also in this embodiment.

Also, in the sensor 3 of this embodiment, the sample can be analyzed by placing a sample or a sample cell in contact with the surface of the first reflecting body 10.

Since, especially the first reflecting body 10 has a recessed/projected structure smaller than the wavelength of the measuring light L1, the change in the average complex refractive index takes place in the first reflecting body 10 at a higher sensitivity for the same reason in the first embodiment. Accordingly, it is preferred that the sample be analyzed with the sample brought into contact at least with the first reflecting body 10.

The pitches of the metal particles 13 may be any so long as they are smaller than the wavelength of the measuring light L1 and when visible light is employed as the measuring light L1, the pitches of the metal particles 13 are preferably not larger than, for instance, 200 nm. The pitches of the metal particles 13 are preferably as small as possible from the viewpoint of sensitivity.

The diameter of the metal particles 13 may be any and are preferably as small as possible from the viewpoint of sensitivity. The diameter of the metal particles 13 is preferably not larger than an average free stroke of the electrons which are vibrated in metal by light, and specifically, is preferably not larger than 50 nm and more preferably not larger than 30 nm.

It is preferred that the pitches and the diameter of the metal particles 13 be preferably as small as possible as in the fine metal cable 11 of the first embodiment, since the proportion of the surface shared by a single metal particle 13 is relatively increased, and the surface characteristics of the metal particles 13 are more apt to be reflected to the general characteristics of the first reflecting body 10, whereby a higher sensitivity can be obtained.

In this embodiment as in the first embodiment, light entering the transparent body 20 after passing through the first reflecting body 10 is repeatedly reflected between the first and second reflecting bodies 10 and 30 to generate a multiple interference due to a multiple reflection, and absorption characteristics where, a particular wavelength satisfying the resonant conditions are selectively absorbed, are exhibited. Further, the local plasmon resonance due to fine metal recessed/projected structure is generated on the surface of the optical resonator (the first reflecting body 10). Since the resonant wavelength λr by the multiple interference can be easily changed by changing the thickness d of the transparent body 20, by causing the resonant wavelength λr and the local plasmon resonant wavelength λ1p to conform to each other by changing the thickness d of the transparent body 20, an emitted light L2 having a reflection peak Prf due to the local plasmon resonance is emitted from the first reflecting body 10.

Also in this embodiment, when the sample is brought into contact with the first and/or second reflecting bodies 10 and 30 (preferably the first reflecting body 10), the average complex index (effective complex index) of the reflecting body in contact with the sample changes by the mutual action of the reflecting body and the sample, and the resonant conditions of the sensor 1 and the local plasmon resonant conditions change, whereby absorption characteristics change and when the absorption characteristics change, the physical properties of the emitted light L2 also change according to the absorption characteristics of the sensor 3. Accordingly, by detecting the physical properties of the emitted light L2, the sample can be analyzed.

The sensor 3 of this embodiment is arranged as described above.

The sensor 3 of this embodiment is basically the same as the first embodiment except that the first reflecting body 10 comprises a metal layer and accordingly, exhibits the same effect as the first embodiment.

Though the case where the first reflecting body 10 comprises a metal layer where a plurality of substantially the same diameter metal particles 13 are regularly arranged in a matrix has been described in this embodiment, the first reflecting body 10 may be distributed and may be in any pattern. The first reflecting body 10 may be even in a random pattern. Further, though the case where the second reflecting body 30 comprises a solid metal layer has been described, the second reflecting body 30 may comprise a metal particle layer as the first reflecting body 10. When such an arrangement is employed, the second reflecting body 30 has a semi-transmissivity/semi-reflectivity, analysis can be done in the manner as the second embodiment.

Fourth Embodiment of the Sensor

Figure 5:
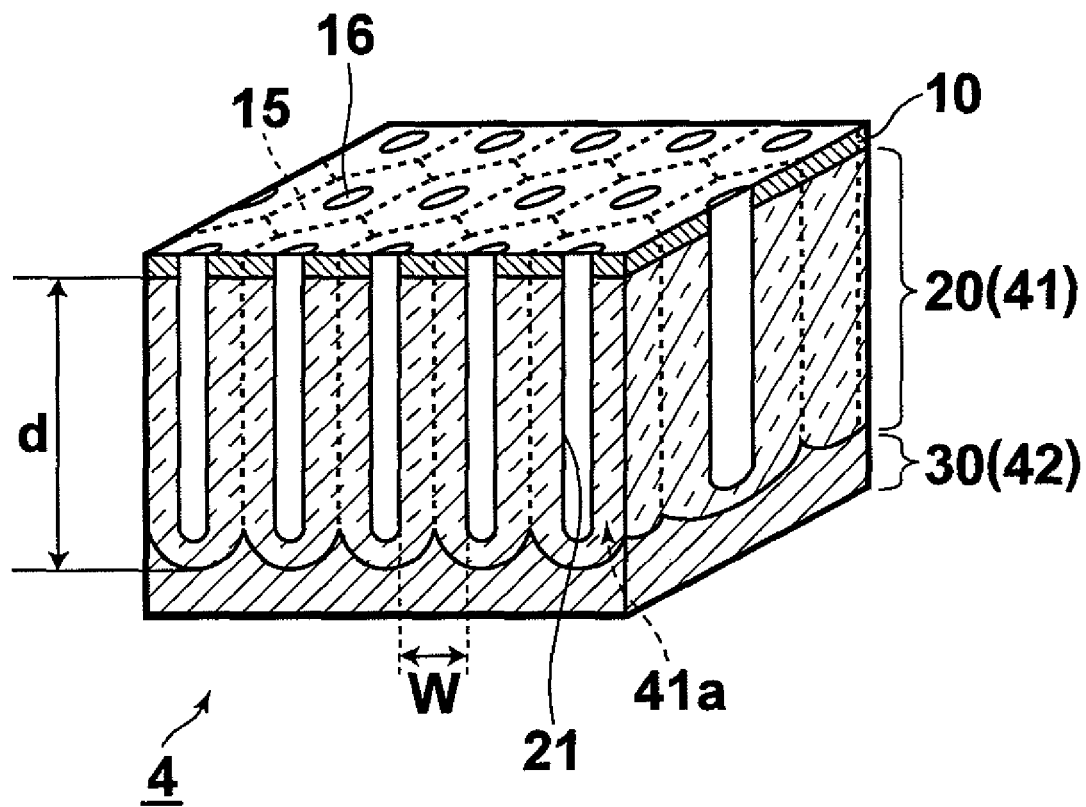
FIG. 5 is a perspective view of a sensor in accordance with a fourth embodiment of the present invention.
Figure 6A:
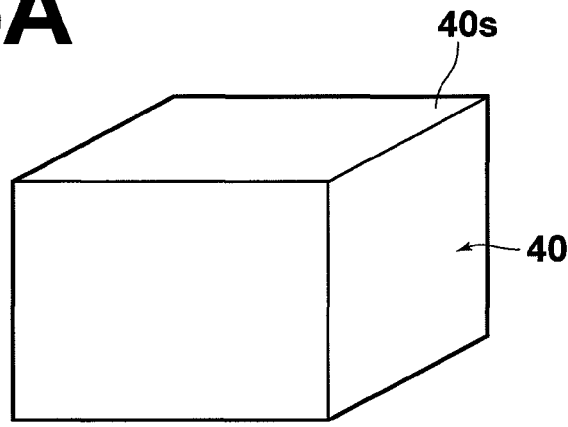
FIGS. 6A to 6C are views showing the process of producing the sensor shown in FIG. 5, FIGS. 7A to 7C are views showing the sensing systems in accordance with a first embodiment of the present invention.
Figure 6B:
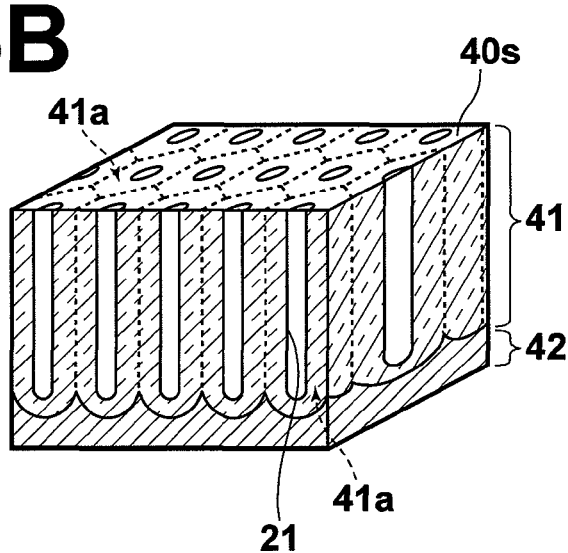
Figure 6C:
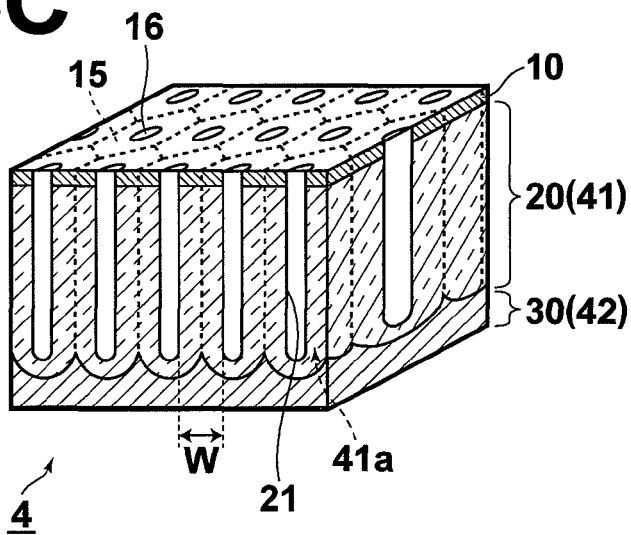

A sensor of a fourth embodiment of the present invention will be described with reference to FIGS. 5 and 6A to 6C, hereinbelow. FIG. 5 is a perspective view of the sensor and FIGS. 6A to 6C are views showing the process of producing the sensor shown in FIG. 5. In this embodiment, the elements analogous to those in the first embodiment will be given the same reference numerals and will not be described.

As shown in FIG. 5, the sensor 4 in accordance with this embodiment comprises similarly to the first embodiment, in sequence from the incident side (from upward in FIG. 3) of measuring light L1, a first reflecting body 10 which exhibits semi-transmissivity/semi-reflectivity, a transparent body 20 and a second reflecting body 30 which has a reflectivity.

In this embodiment, different from the first embodiment, the transparent body 20 is formed of metal oxide ($Al_2O_3$) 41 obtained by anodic-oxidizing a part of metal to be anodic oxidized (Al) 40 shown in FIG. 6A and the second reflecting body 30 is formed of a non-anodic-oxidized part (Al) 42 of the metal to be anodic oxidized 40 shown in FIG. 6A. The second reflecting body 30 has a reflectivity.

The transparent body 20 is a light transmitting fine hole body provided with a plurality of substantially straight fine holes 21 extending from the first reflecting body side to the second reflecting body side. The plurality of fine holes 21 are open at the face on first reflecting body side and are closed at the face on second reflecting body side. In the transparent body 20, each of the plurality of fine holes 21 has a diameter smaller than the wavelength of the measuring light L1 and the plurality of fine holes 21 are arranged substantially regularly at pitches smaller than the wavelength of the measuring light L1.

The anodic oxidation can be carried out by dipping the metal to be anodic oxidized 40 (as the anode) in an electrolysis solution together with the cathode, and imparting an electric voltage across the anode and the cathode. Though the shape of the metal to be anodic oxidized 40 is not limited, it is preferred that the metal to be anodic oxidized 40 be like a plate or the like in shape. Those with a supporter such as those where films of metal to be anodic oxidized 40 is formed on a supporting body in layers may be used. As the cathode, for instance, carbon or aluminum is used. As the electrolysis solution, an acidic electrolysis solution including but not limited to one or more of sulfuric acid, phosphoric acid, chromic acid, oxalic acid, sulfamic acid, benzenesulfonic acid or amidosulfonic acid may be preferably used.

As shown in FIGS. 6A to 6C, when anodic-oxidizing metal to be anodic oxidized 40, the oxidization progresses from a surface 40s substantially in perpendicular to the surface 40s and metal oxide ($Al_2O_3$) 41 is formed. The metal oxide 41 formed by the anodic oxidation is of structure where number of fine columns 41a regular hexagonal in plan are arranged without a space therebetween. At substantially the center of each fine column 41a, the fine hole 21 extending substantially straight in the direction of depth from the surface 40s opens, and the base of each fine column 41a is rounded in shape. The structure of the metal oxide body formed by the anodic oxidation is disclosed, for instance, in "Preparation of mesoporous Alumina by Anode Oxidation and Application thereof to functional Material" by H. Masuda, Material Technology, Vol. 15, No. 10, p. 34, 1997.

As suitable conditions under which the anode-oxidation is to be carried out to form the regularly arranged metal oxide body 41, conditions, for instance, that the concentration of the electrolysis solution is 0.5M, the temperature of the electrolysis solution is 14 to 16° C., and the electric voltage to be imparted across the anode and the cathode is 40 to 40±0.5 V when oxalic acid is employed as the electrolysis solution can be shown. The fine holes 21 formed under these conditions are 5 to 200 nm in diameter and 10 to 400 nm in pitches.

In this embodiment, the first reflecting body 10 is formed by, for instance, metal deposition to the transparent body 20 and comprises a metal layer formed along the surface contour of the transparent body 20. Since, no metal film is formed in the part of the transparent body in which the fine holes 21 open, the first reflecting body 10 is of structure where number of fine metal bodies 15 each of which has a fine hole 16 at substantially the center thereof and is a regular hexagon in plan are arranged without a space therebetween. Since fine holes 16 of the first reflecting body 10 is formed in the same pattern as the fine holes 21 of the transparent body 20, each of the plurality of fine holes 16 has a diameter smaller than the wavelength of the measuring light L1 and the plurality of fine holes 16 are arranged substantially regularly at pitches smaller than the wavelength of the measuring light L1.

The first reflecting body 10 exhibits a light transmissivity since it has a plurality of fine holes 16 each of which is a vacant spaces though formed of reflective metal and after all exhibits a semi-transmissivity/semi-reflectivity. Since comprising number of substantially regularly arranged fine metal bodies 15 each of which has a fine hole 16 at substantially the center thereof, is smaller than the wavelength of the measuring light L1 and is regular hexagonal in plan, the first reflecting body 10 has a recessed/projected structure (sometimes referred to as "an irregularity") smaller than the wavelength of the measuring light L1. Since the recessed/projected structure is smaller than the wavelength of the light, the first reflecting body 10 behaves as film to light and exhibits a semi-transmissivity/semi-reflectivity by a so-called electromagnetic mesh shielding effect also in this embodiment.

Also the sensor 4 of this embodiment is a sensor where average complex refractive indexes of the first and second reflecting bodies 10 and 30 change according to the sample in contact with the first and second reflecting bodies 10 and 30 and the sample can be analyzed by placing a sample in contact with the first and/or second reflecting bodies 10 and 30.

Since, the first reflecting body 10 has a recessed/projected structure formed by fine metal bodies 15 regular hexagonal in plan smaller than the wavelength of the measuring light L1, the change in the average complex refractive index takes place in the first reflecting body 10 at a higher sensitivity for the same reason in the first embodiment. Accordingly, it is preferred that the sample be analyzed with the sample brought into contact at least with the first reflecting body 10.

The pitches of the metal bodies 15 (pitches of the fine holes 16) may be any so long as they are smaller than the wavelength of the measuring light L1 and when visible light is employed as the measuring light L1, the pitches of the metal bodies 15 are preferably not larger than, for instance, 200 nm. The pitches of the metal bodies 15 are preferably as small as possible from the viewpoint of sensitivity.

Spaces between adjacent fine holes 16 (the width W of metal bodies 15 between adjacent fine holes 16) may be any and is preferably as small as possible from the viewpoint of sensitivity. The width W corresponds to the width of the fine metal cable 11 and diameter of the metal particles 13 in the first and third embodiments. The width W is preferably not larger than an average free stroke of the electrons which are vibrated in metal by light, and specifically, the width W is preferably not larger than 50 nm and more preferably not larger than 30 nm.

It is preferred that the pitches and the width of the metal body 15 be preferably as small as possible as in the fine metal cable 11 in the first embodiment, since the surface characteristics of the metal particles 13 are more apt to be reflected to the general characteristics of the first reflecting body 10, whereby a higher sensitivity can be obtained.

In the sensor 4 of this embodiment, since the second reflecting body 30 is formed of a non-anodic-oxidized part (Al) 42 of the metal to be anodic oxidized 40, the second reflecting body 30 is provided with fine irregularities on the surface thereof. Accordingly, different from the first and third embodiments, the local plasmon resonance takes place also in the second reflecting body 30 having a reflectivity.

In the sensor 4 of this embodiment, it is preferred that metal be loaded on the bottom of the fine holes 21. The metal loaded on the bottom of the fine holes 21 may be deposited on the bottom of the fine holes 21 when the first reflecting body 10 is formed. In this case, since the metal is loaded on the bottom of fine holes 21 which are formed in the fine columns 41*a* of the light transmissible metal oxide and are substantially regularly arranged in the device, a more effective local plasmon resonance takes place in the device and a more sensitive measurement can be done.

The metal loaded on the bottom of the fine holes 21 may be any so long as it is metal as the first reflecting body, and is preferably gold (Au), silver (Ag), copper (Cu), nickel (Ni) or titanium (Ti) and gold (Au) and silver (Ag) is especially preferable. In this case, since a local plasmon resonance takes place on the surface of the first reflecting body and on the bottom of the fine holes 21, it is preferred that metal loaded on the bottom of the fine holes 21 be of the same kind as the metal of the first reflecting body 10 in order to obtain a more effective local plasmon resonance.

As in the first embodiment, also in this embodiment, light which passes through the first reflecting body 10 and enters the transparent body 20 is repeatedly reflected between the first and second reflecting bodies 10 and 30 and a multiple interference by multiple reflection light takes place and resonates at a particular wavelength satisfying the resonant conditions. By the resonance, absorption characteristics are exhibited where light of a particular wavelength satisfying the resonant conditions is selectively absorbed. On the surface and the inside of the optical resonator (the first and second reflecting body 10 and 30), the local plasmon resonance is generated due to fine irregularities on the surface thereof. Since the resonant wavelength λr by the multiple interference can be easily changed by changing the thickness d of the transparent body 20 also in this embodiment, by causing the resonant wavelength λr and the local plasmon resonant wavelength λ1$p$ to conform to each other by changing the thickness d of the transparent body 20, an emitted light L2 having a reflection peak Prf due to the local plasmon resonance is emitted from the first reflecting body 10.

When the sample is brought into contact with the first and/or second reflecting bodies 10 and 30 (preferably, the first reflecting body 10), the average complex index (effective complex index) of the reflecting body in contact with the sample changes by the mutual action of the reflecting body and the sample and the resonant conditions of the sensor 4 and the local plasmon resonant conditions change, whereby absorption characteristics change. Since the physical properties of the emitted light L2 change with the absorption characteristics of the sensor 4, by detecting the physical properties of the emitted light L2, the sample can be analyzed.

The sensor 4 of this embodiment is arranged as described above.

The sensor 4 of this embodiment is basically the same as the first embodiment except that the transparent body 20 comprises a light transmissible fine hole member having a plurality of fine holes 21 open in the face facing the first reflecting body 10 and the first reflecting body 10 comprises a metal layer formed along the surface contour of the transparent body 20 and accordingly, exhibits the same effect as the first embodiment.

Since being produced on the basis of the anodic oxidation, the sensor 3 of this embodiment is preferred in that a sensor 4 where the fine holes 21 of the transparent body 20 and the fine holes 16 of the first reflecting body 10 are substantially regularly arranged can be easily produced. However, these fine holes may be randomly arranged.

Though metal is filled in only the bottom of the fine holes 21 in this embodiment, it is possible to fill metal in the larger part inside the fine holes 21. However, in this case, the amount of metal to be loaded should be in the range where light which passes through the first reflecting body 10 and enters the transparent body 20 is repeatedly reflected between the first and second reflecting bodies 10 and 30 and a multiple interference by multiple reflection light takes place.

Though as a main component of the metal to be anodic oxidized 40 used in production of the transparent body 20, only Al is shown in this embodiment, any metal can be used so long as it can be anodic-oxidized and the metal oxide to be generated is light transmissible. Other than Al, Ti, Ta, Hf, Zr, Si, In, Zn or the like may be used. The metal to be anodic oxidized 40 may include two or more kinds of metals which can be anodic-oxidized.

Though the case where the first reflecting body 10 has a reflectivity has been described in this embodiment, a transparent body 20, where the fine holes 21 extend through the transparent body 20, can be obtained by wholly anodic-oxidizing metal to be anodic oxidized 40 or by anodic-oxidizing a part of metal to be anodic oxidized 40 and removing the non-anodic-oxidized part 42 of the metal to be anodic oxidized 40 and near thereto. When forming the second reflecting body 30 along the surface contour of the transparent body 20, a second reflecting body 30 having semi-transmissivity/semi-reflectivity as the first reflecting body 10 can be produced and a sample analysis can be done as in the second embodiment.

Example of the Design Change

In the sensor of this invention, the first and second reflecting bodies 10 and 30 may be changed in the arrangements thereof and the combination thereof. For example, the sensor of this invention may be arranged by combining the first and second reflecting bodies 10 and 30 of the first to fourth embodiments.

Sensing System

Sensing systems in accordance with first to fourth embodiments of the present invention will be described with reference to FIGS. 7A to 7C. Through the examples, the reflective sensors or the semi-transmitting/semi-reflective sensors are employed.

Figure 7A:
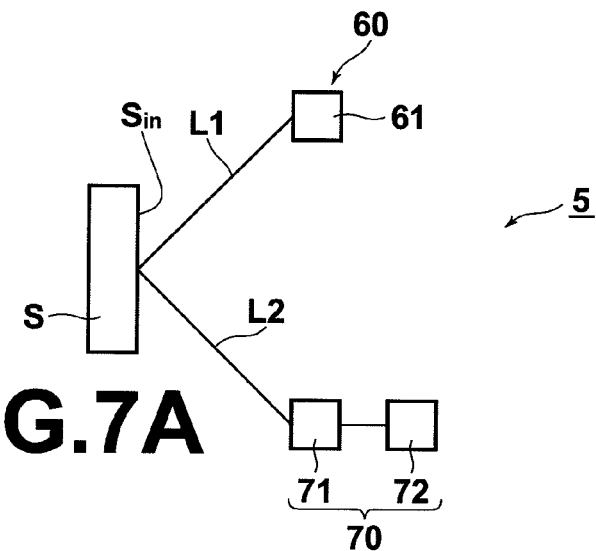
Figure 7B:
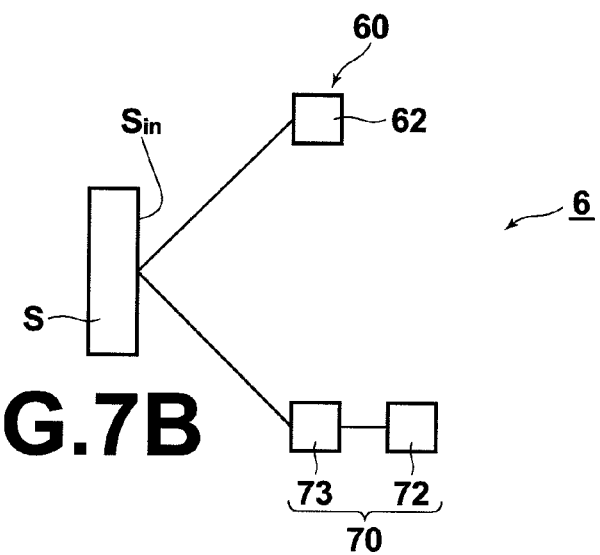
Figure 7C:
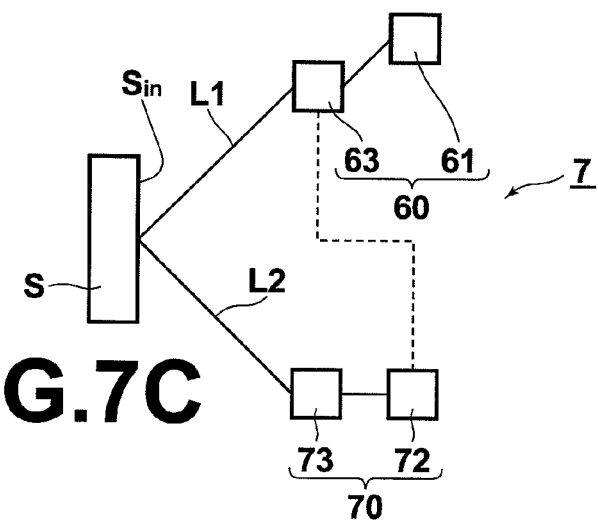

Sensing systems 5 to 7 of embodiments of the present invention shown in FIGS. 7A to 7C comprises a sensor S of the present invention, a measuring light projecting means 60 which projects the measuring light L1 onto the sensor S and a detector 70 which detects physical properties of the reflected light as the emitted light L2, and various combinations of the measuring light projecting means 60 and the detector 70 are employed. Analogous elements are given the same reference numerals. Since the sensing systems 5 to 7 are the reflective sensors, the light inlet surface $S_{in}$ is the same as the light emanating surface and comprises the first reflecting body 10 of the sensor S of the present invention.

Since the sensors of the present invention emit emitted light L2 having a reflection peak Prf peculiar to the device structure as described above in conjunction with the first to fourth embodiments of the present invention described above, the sensing systems using the sensors of the present invention carries out the analysis of the sample by detecting at least one of the intensity, the rate of change of the intensity, the reflection peak wavelength $\lambda rf$ and the shift of the reflection peak wavelength $\lambda rf$ of the emitted light L2.

The sensing system 5 is a system, where the measuring light projecting means 60 comprises abroad light source 61 such as a halogen lamp, a xenon lamp or a krypton lamp, and the detector 70 comprises a spectroscopic device 71 and a data processing portion 72. The measuring light projecting means 60 may be provided with an optical waveguide system, if necessary, including a collimator lens and/or a collecting lens for making parallel the light emanating from the light source 61.

The sensing system 5 analyzes the sample (the spectrum and the reflection peak are referred to FIG. 2C) by projecting broad light (as the measuring light L1) onto the sensor S with the measuring light projecting means 60 and by obtaining the spectrum of the reflected light which is the emitted light L2 and detecting the reflection peak wavelength $\lambda rf$ of the emitted light L2 and the shift of the reflection peak wavelength $\lambda rf$ of the emitted light L2 from that obtained under the reference conditions changing with the light absorption characteristics of the sensor with the detector 70.

The sensing system 6 is a system, where the measuring light projecting means 60 comprises a mono-wavelength light source 62 such as a laser or a light emitting diode, and the detector 70 comprises a light intensity detector 73, such as a photodiode, and a data processing portion 72. Also in the sensing system 6, the measuring light projecting means 60 may be provided with an optical waveguide system, if necessary, including a collimator lens and/or a collecting lens for making parallel the light emanating from the light source 61.

The sensing system 6 analyzes the sample by projecting mono-wavelength light (as the measuring light L1) onto the sensor S with the measuring light projecting means 60 and by detecting the intensity of the reflected light which is the emitted light L2 with the detector 73. The sample can be analyzed by detecting the intensity of the emitted light L2 for the measuring light L1 of any wavelength since the intensity of the emitted light of any wavelength changes. However, the sample can be analyzed at a high sensitivity when a wavelength near the reflection peak wavelength $\lambda rf$ is used.

In the sensing system 6, a similar sample analysis can be carried out by the use of the measuring light projecting means 60 comprising a broad light source 61 and a wavelength distribution changing means 63 such as a spectroscope which takes out only light of a particular wavelength from light emitted from the light source 61 instead of using the mono-wavelength light source 62.

The sensing system 7 is a system, where the measuring light projecting means 60 comprises abroad light source 61 and a wavelength distribution changing means 63 such as a spectroscope which takes out only light of a particular wavelength from light emitted from the light source 61 and can change with time the wavelength of light taken out from the light source 61, and the detector 70 comprises a light intensity detector 73 and a data processing portion 72. Into the data processing portion 72, wavelength data on the light of a particular wavelength taken out from the wavelength distribution changing means 63 and intensity data on the intensity of light by the light intensity detector 73 are input and processed. Also in the sensing system 7, the measuring light projecting means 60 may be provided with an optical waveguide system, if necessary, including a collimator lens and/or a collecting lens.

The sensing system 7 analyzes the sample by projecting mono-wavelength light (as the measuring light L1) onto the sensor S and changing the wavelength with time of the mono-wavelength light to be projected onto the sensor S with the measuring light projecting means 60 and by measuring with time the intensity of the reflected light which is the emitted light L2 with the detector 73 to obtain the spectrum similar to that shown in FIG. 2C, thereby detecting the reflection peak wavelength λrf of the emitted light L2 or the shift of the reflection peak wavelength λrf of the emitted light L2 from that obtained under the reference conditions.

As described above by way of examples, the sample can be analyzed by detecting at least one of the intensity, rate of change of the intensity, the reflection peak wavelength λrf and the shift of the reflection peak wavelength λrf from that obtained under the reference conditions of the emitted light L2.

In the sensing systems 5 to 7, the refractive index and/or the concentration of a sample can be analyzed and the sample can be even identified by analyzing the refractive index of the sample. Further, existence and/or a quantity of the specific material in the sample can be analyzed by bringing a sample into contact with a sensor S after bringing a bonding material which specifically bonds with specific material into contact with a contact side of the sensor S, projecting measuring light L1 onto the sensor S and detecting the emitted light L2.

Further, the reflective sensing systems 5 to 7 is preferred that the detector 70 receives only the non-direct-reflection components of the emitted light L2 emitted from the first reflecting body 10 of the sensor S and detects the physical properties of the emitted light L2. The direct-reflection components are strong in intensity, and there is a fear that the S/N ratio of the physical properties of the emitted light to be intrinsically detected is lowered and the detecting accuracy is lowered when the direct-reflection components are included in the emitted light L2 to be detected.

For a similar reason, in the reflective sensing systems 5 to 7, it is preferred that the measuring light projecting means 60 be positioned to project the measuring light L1 onto the sensor S from a direction not at 90° to the light incident surface $S_{in}$ (first reflecting body 10) of the sensor S.

Though only the reflective sensing systems are described, the transmitting sensing systems which are provided with a transmitting sensor or a semi-transmitting/semi-reflective sensor and for detecting transmitted light have only to be arranged so that the detector 70 detects transmitted light by, for instance, positioning the detector 70 toward the second reflecting body 30.

Embodiments

Embodiment 1

The spectrum obtained from the sensors of the present invention when white light is employed as the measuring light is simulated in electromagnetic field analysis simulation by the FDTD method to prove the spectrum change before and after adsorption of the sample. As a model for use in the simulation, the sensor 4 of the fourth embodiment was employed.

Figure 8A:
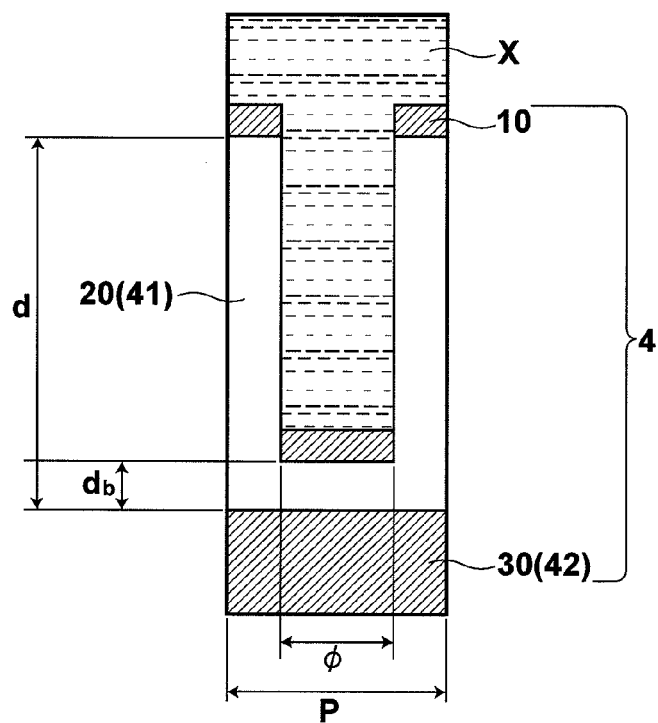
FIG. 8A is an enlarged cross-sectional view of the sensor in accordance with the fourth embodiment of the present invention.

FIG. 8A is a cross-sectional view in the direction of depth of the sensor 4 employed as the model, and in FIG. 8A, one fine column is shown in an enlarged scale for the purpose of simplicity in viewing the simulating conditions. Since the general arrangement of the sensors 4 employed as the model are shown in FIG. 3, elements analogous to those shown in FIG. 3 are given the same reference numerals and are not described.

As shown in FIG. 8A, in the sensors employed as a model, the metal to be anodic oxidized 40=A1, the diameter φ of the fine holes 21=50 nm, pitches P=100 nm, the first reflecting body 10=Au, the thickness of the deposited first reflecting body=20 nm, the thickness d of the transparent fine hole body ($Al_2O_3$) 41=400 nm, and the thickness db of the bottom $Al_2O_3$=20 nm, and metal Au the same as the first reflecting body 10 was deposited on the bottom of the fine holes 21 in the thickness of 20 nm and the sample in contact with the sensor was those obtained by dispersing, in water, adsorbing material whose refractive index was 1.7.

In the simulation, the reflectance of the emitted light when mono-wavelength light at an arbitrary wavelength was caused to enter the surface of the first reflecting body in substantially perpendicularly thereto were calculated to prove the absorption characteristics of the emitted light from the sensor 4. The result is shown in FIG. 8B.

Figure 8B:
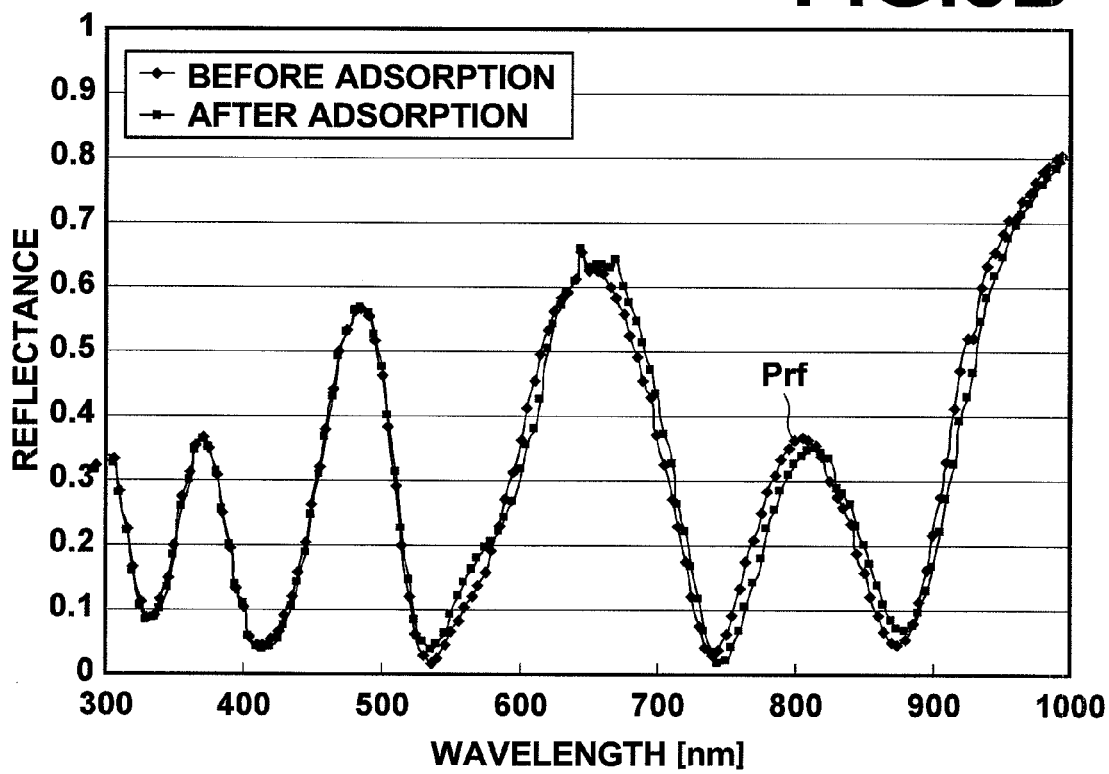
FIG. 8B is a view showing emitted light absorption characteristics of the embodiment 1.

FIG. 8B is obtained by plotting the reflectance of emitted light from the surface of the sensor 4 (the first reflecting body 10) at each wavelength and shows the absorption characteristics of the sensor.

In the illustrated spectra, the reflection peak which appears by virtue of the sensor arrangement of the present invention is a peak appearing near 800 nm. The reflection peak arises substantially from the zero base, and it has been confirmed that sensing using a peak which is high in S/N ratio is realized by the sensors of the present invention. Further, since the amount of shift of the spectrum between before and after adsorption is large as compared with other peaks, it is found that by the sensors of the present invention, sensing can be carried out at an excellent sensitivity.

The sensors of the present invention can be suitably used, for instance, as a biosensor.

The invention claimed is:

1. A sensor that receives a measuring light beam incident into a sample, and outputs an emitted light beam having different physical properties depending on the sample, in the form of an optical resonator, comprising:

a first reflecting body that exhibits semi transmissivity/semi reflectivity, wherein the first reflecting body, which is placed into contact with the sample, has a structure of protrusions and recesses, which are smaller than the wavelength of the measuring light beam;

a transparent body; and a second reflecting body that exhibits one of reflectivity and semi transmissivity/semi reflectivity, provided in this order from the light incident side, wherein the average complex refractive index n2−ik2 and the thickness d of the transparent body together with the resonant wavelength λr sufficiently satisfy the following formula at the order of several nm, and so long as the average complex refractive index n2−ik2 of the transparent body is the same, the resonant wavelength λr can be changed by simply changing the thickness d of the transparent body such that the absorption peak of the measuring light beam by resonance in the optical resonator matches the absorption peak of the measuring light beam by local plasmon resonance generated at the surface and/or within the optical resonator, $$D=(m+1)\lambda r/2\ (n2-ik2)$$

wherein d represents the thickness of the transparent body, λr represents the resonant wavelength, n2−ik2 represents average complex refractive index and m represents an integer.

2. A sensor as defined in claim 1, wherein:
the second reflecting body, which is placed into contact with the sample, has a structure of protrusions and recesses, which are smaller than the wavelength of the measuring light beam.

3. A sensor as defined in claim 2, wherein:
the first reflecting body and/or the second reflecting body, which is placed into contact with the sample, is a metal layer formed in a pattern on the surface of the transparent body.

4. A sensor as defined in claim 2, wherein:
the first reflecting body and/or the second reflecting body, which is placed into contact with the sample, is a metal layer comprising a plurality of non-aggregate metal particles which are fixed to the surface of the transparent body.

5. A sensor as defined in claim 2, wherein:
the transparent body is a transparent finely apertured body having a plurality of fine apertures which are open in a surface facing the first reflecting body and of which the diameters are smaller than the wavelength of the measuring light beam in diameter; and
the first reflecting body is a metal layer having a plurality of fine apertures along the shape of the surface of the transparent body.

6. A sensor as defined in claim 5, wherein:
the transparent finely apertured body is a metal oxide body obtained by anodic oxidization of a part of a metal body;
the second reflecting body is a non anodic oxidized part of the anodic oxidized metal body; and
the first reflecting body is a metal layer formed as a film on the transparent body.

7. A sensor as defined in claim 5, wherein:
at least a portion of the plurality of fine apertures of the transparent finely apertured body is filled with metal.

8. A sensor as defined in claim 7, wherein:
the bottoms of the plurality of fine apertures of the transparent finely apertured body are filled with metal.

9. A sensing apparatus, comprising:
a sensor as defined in claim 1;
a light emitting means for emitting the measuring light beam onto the sensor; and
a detector that detects the physical properties of the emitted light beam, which is output from the sensor.

10. A sensing apparatus as defined in claim 9, wherein:
the detector detects at least one of the intensity, the rate of change of the intensity, the reflection peak wavelength and the reflection peak wavelength shift of the emitted light beam, which is output from the sensor.

11. A sensing apparatus as defined in claim 9, wherein:
the emitted light beam is output from at least the first reflecting body of the sensor; and
the detector receives and detects the physical properties of only the non directly reflected components of the emitted light beam output from the first reflecting body.

12. A sensing apparatus as defined in claim 9, wherein:
the light emitting means is positioned to emit the measuring light beam onto the light incident surface of the sensor from a direction not perpendicular thereto.

13. A sensing method, comprising the steps of:
bring the sample into contact with a sensor as defined in claim 1, after immobilizing a binding substance that specifically binds with a specific substance onto a contact side of the sensor,
emitting the measuring light beam onto the sensor; and
detecting the physical properties of the emitted light beam output from the sensor, to analyze the presence and/or a quantity of the specific substance in the sample.

14. A sensor as defined in claim 1, wherein:
the physical properties depending on the sample are at least one of the intensity, the rate of change of the intensity, the reflection peak wavelength and the reflection peak wavelength shift.

\* \* \* \* \*